United States Patent
Gordon et al.

(10) Patent No.: US 8,640,906 B2
(45) Date of Patent: Feb. 4, 2014

(54) MULTIPURPOSE COOKING STOVE CONTAINER

(75) Inventors: Cathal Patrick Gordon, Coppersburg, PA (US); David Dean McClanahan, Harleysville, PA (US)

(73) Assignee: Cathal Patrick Gordon, Coppersburg, PA (US)

( * ) Notice: Subject to any disclaimer, the term of this patent is extended or adjusted under 35 U.S.C. 154(b) by 230 days.

(21) Appl. No.: 13/068,635

(22) Filed: May 17, 2011

(65) Prior Publication Data

US 2011/0284546 A1    Nov. 24, 2011

(51) Int. Cl.
*B65D 25/22*    (2006.01)
*A47J 47/00*    (2006.01)
*F24C 15/18*    (2006.01)

(52) U.S. Cl.
USPC ........... 220/476; 220/480; 220/482; 248/214; 248/215; 248/315; 248/206.1; 248/309.1; 126/41 R; 126/25 R; 206/228

(58) Field of Classification Search
USPC ....... 220/480, 482; 312/236; 126/41 R, 25 R, 126/38, 9 R, 125, 276; D7/402.404, 406; 206/225; 248/206.1, 309.1, 309.4, 248/206.5, 689, 225.11, 125.2, 214, 215; 99/357, 484; 114/347, 364, 343; 224/570
See application file for complete search history.

(56) References Cited

U.S. PATENT DOCUMENTS

| | | | | |
|---|---|---|---|---|
| 2,304,312 A | * | 12/1942 | Meglitz | 225/47 |
| 2,661,258 A | * | 12/1953 | Dinken | 312/248 |
| 2,711,213 A | * | 6/1955 | Owens | 248/231.81 |
| 3,409,340 A | * | 11/1968 | Clark | 312/34.8 |
| 3,476,346 A | * | 11/1969 | Oakes | 5/430 |
| 3,846,005 A | * | 11/1974 | Harper et al. | 312/248 |
| 3,951,486 A | * | 4/1976 | Tracy | 312/235.8 |
| 4,059,248 A | * | 11/1977 | Kuntz | 248/214 |
| 4,325,294 A | * | 4/1982 | Hammond | 99/337 |
| 4,337,751 A | * | 7/1982 | Sampson et al. | 126/25 R |
| 4,516,676 A | | 5/1985 | Cournoyer | |
| 4,535,921 A | * | 8/1985 | Sanders | 223/106 |
| 4,665,891 A | * | 5/1987 | Nemec et al. | 126/25 R |
| 4,677,964 A | * | 7/1987 | Lohmeyer et al. | 126/41 R |
| 4,703,850 A | * | 11/1987 | Walker | 206/293 |
| D296,861 S | * | 7/1988 | Fielding et al. | D7/402 |
| 4,787,364 A | * | 11/1988 | Zepeda | 126/41 R |
| 4,895,068 A | * | 1/1990 | Hanagan et al. | 99/357 |
| 4,899,725 A | * | 2/1990 | Barron, Jr. | 126/41 R |
| 5,033,448 A | * | 7/1991 | Sandweg | 126/25 R |
| 5,076,257 A | * | 12/1991 | Raymer et al. | 126/41 R |
| 5,090,398 A | * | 2/1992 | Raymer et al. | 126/41 R |
| 5,228,584 A | * | 7/1993 | Williams, Jr. | 220/3.8 |

(Continued)

*Primary Examiner* — Mickey Yu
*Assistant Examiner* — Gideon Weinerth
(74) *Attorney, Agent, or Firm* — Invention To Patent Services; Alex R Hobson

(57) ABSTRACT

A multipurpose cooking stove container is described having a cavity for storing items such as cleaning products and hand sanitizer. The cooking stove container may further comprise a paper towel support and mounting bracket for attachment to a cooking stove or side shelf of a cooking stove. The cooking stove container may also be configured to be resistant to environmental elements such as rain, wind, dust, pollen and the like. A tray portion may be used for storing items and a removable cup may be inserted into the tray for more secure storage of smaller items. The cooking stove container may in one embodiment comprise a front and back member that are attached about a pivot. The front member may pivot to allow access to the inside cavity.

18 Claims, 15 Drawing Sheets

(56) References Cited

U.S. PATENT DOCUMENTS

| | | | |
|---|---|---|---|
| 5,294,194 A * | 3/1994 | Lombardo | 312/229 |
| 5,310,147 A * | 5/1994 | Billman | 248/214 |
| 5,341,793 A * | 8/1994 | Brown | 126/41 R |
| 5,398,824 A | 3/1995 | Wolff et al. | |
| D362,753 S * | 10/1995 | Bland | D3/260 |
| 5,472,164 A * | 12/1995 | Contee, Jr. | 248/214 |
| 5,800,027 A * | 9/1998 | Dunn | 312/138.1 |
| 5,909,832 A | 6/1999 | French et al. | |
| 5,992,718 A | 11/1999 | Zaranek | |
| 6,135,276 A * | 10/2000 | French et al. | 206/225 |
| 6,367,403 B1 * | 4/2002 | Carter | 114/343 |
| 6,439,222 B1 | 8/2002 | Dixon et al. | |
| 6,474,327 B1 | 11/2002 | Bossler | |
| 6,550,729 B1 * | 4/2003 | Ritter et al. | 248/214 |
| 6,561,178 B1 * | 5/2003 | Hayes | 126/25 R |
| 6,691,897 B2 | 2/2004 | Ashe | |
| D522,310 S * | 6/2006 | Nipke | D7/402 |
| 7,222,747 B1 | 5/2007 | Savran | |
| 7,739,964 B2 * | 6/2010 | Hatton | 108/47 |
| 2006/0091146 A1 * | 5/2006 | Boulet-Mazer | 221/34 |
| 2009/0266856 A1 * | 10/2009 | Ponce et al. | 224/401 |
| 2009/0289137 A1 | 11/2009 | Fischer | |
| 2011/0271950 A1 * | 11/2011 | Nilssen, II | 126/25 R |
| 2013/0174771 A1 * | 7/2013 | Teague | 114/343 |

* cited by examiner

US 8,640,906 B2

MULTIPURPOSE COOKING STOVE CONTAINER

CROSS REFERENCE TO RELATED APPLICATIONS

This application claims the benefit of U.S. Provisional Patent Application Number 61/347,512, filed on May 24, 2010, which is incorporated herein by reference in its entirety.

BACKGROUND OF THE INVENTION

1. Field of the Invention

This invention relates generally to containers, uses of containers, and methods of fabrication and use of containers.

2. Background

The first step many people take before cooking on a grill is to clean the cooking surface. It is inconvenient to carry the cleaning supplies and paper towels out to the grill and then there is little area to place them after you are finished cleaning. In addition, paper towels are typically necessary throughout the cooking process and can be difficult to manipulate when not retained by a support. Furthermore, often a person will come into contact with raw meat during the grilling process, and may need or want to sanitize their hands before touching plates, utensils, the handle of the grill and the like. Again, people may find it burdensome to have to go inside each time it is necessary to wash or sanitize their hands. Many barbeque grills do not have a storage container and some that do, do not necessarily have water resistant containers. There exists a need for a container that can be mounted to a grill that is capable of storing cleaning supplies paper towels and the like. In addition, there exists a need for this container to be water resistant.

SUMMARY OF THE INVENTION

The invention is directed to a multipurpose cooking stove container that can store items that may be useful during grilling, including but not limited to, cleaning supplies, hand sanitizer, paper towels, cooking accessories such as spices, or utensils, and the like. In one embodiment, the cooking stove container is connected with a grill tray or side shelf and in an alternative embodiment, the cooking stove container is part of a grill. In another embodiment, the cooking stove container may comprise a mounting device that allows the cooking stove container to be detachably attached to the grill.

The multipurpose cooking stove container comprises a back member and a front member that are configured to create a cavity wherein items may be stored. In some embodiments, the back member and front member are configured such that at least one member can be opened to provide access to the cavity. For example in one embodiment, the back and front member are connected at a pivot point, whereby at least one member can pivot about the pivot to allow access to the cavity. In another embodiment, a moveable connection, hinge or seam may allow a portion of one of the members to be opened, thereby allowing access to the cavity.

The multipurpose cooking stove container may further comprise a tray for convenient storage of items. The tray may be further configured to accept a cup or cups that may seat into or on the tray and in some cases may be slid along the tray for adjustable storage configurations. The cup may allow for more convenient storage and accessibility to smaller or shorter items. In addition, the cooking stove container may be configured with an opening that allows access to the cavity without opening the cavity completely. For example, an opening may be on a side panel and may provide access to hand sanitizer. In another embodiment, a cover may be positioned over the cavity opening and may be slid or moved out of the way to provide access to the cavity opening.

The cooking stove container may be configured in such a way to protect the contents within the container cavity from environmental elements such as rain, wind, dirt, pollen and the like. The top of the back member may extend over the front member when in the closed position, thereby protecting the cavity from the elements. In addition, a portion of the front member may nest within the back member.

The cooking stove container may comprise a towel roll support and may also have a towel opening whereby the towels can be accessed without opening the container.

BRIEF DESCRIPTION OF THE DRAWINGS

The accompanying drawings are included to provide a further understanding of the invention and are incorporated in and constitute a part of this specification, illustrate embodiments of the invention; and together with the description serve to explain the principles of the invention.

DETAILED DESCRIPTION OF THE ILLUSTRATED EMBODIMENTS

Figure 1:
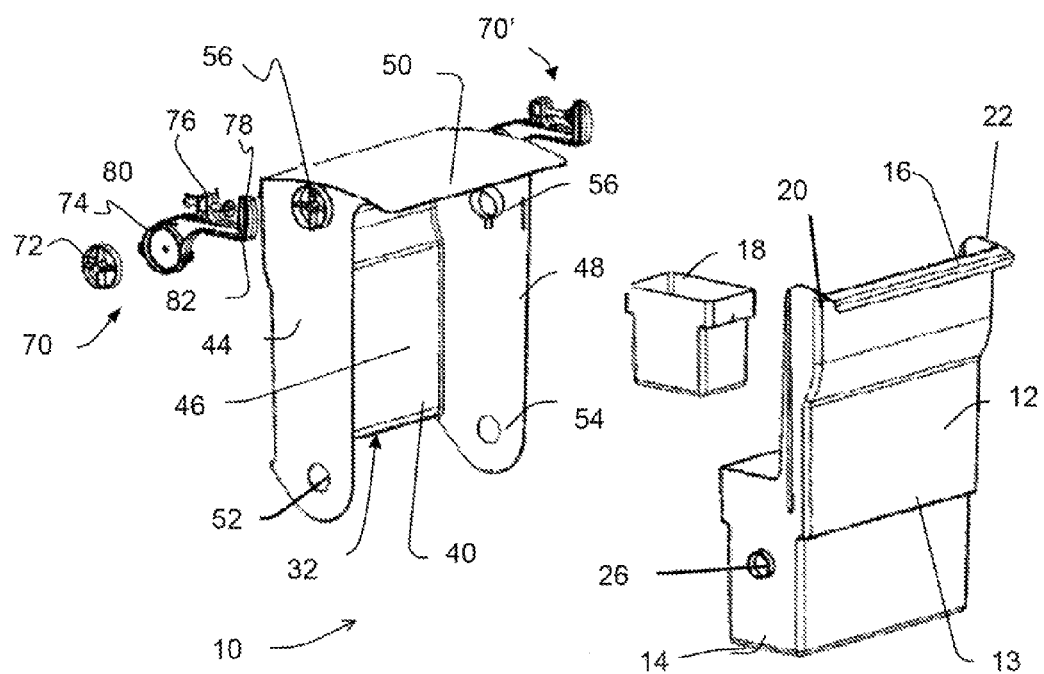

FIG. 1 shows an isometric exploded view of an embodiment of a cooking stove container.

Figure 2:
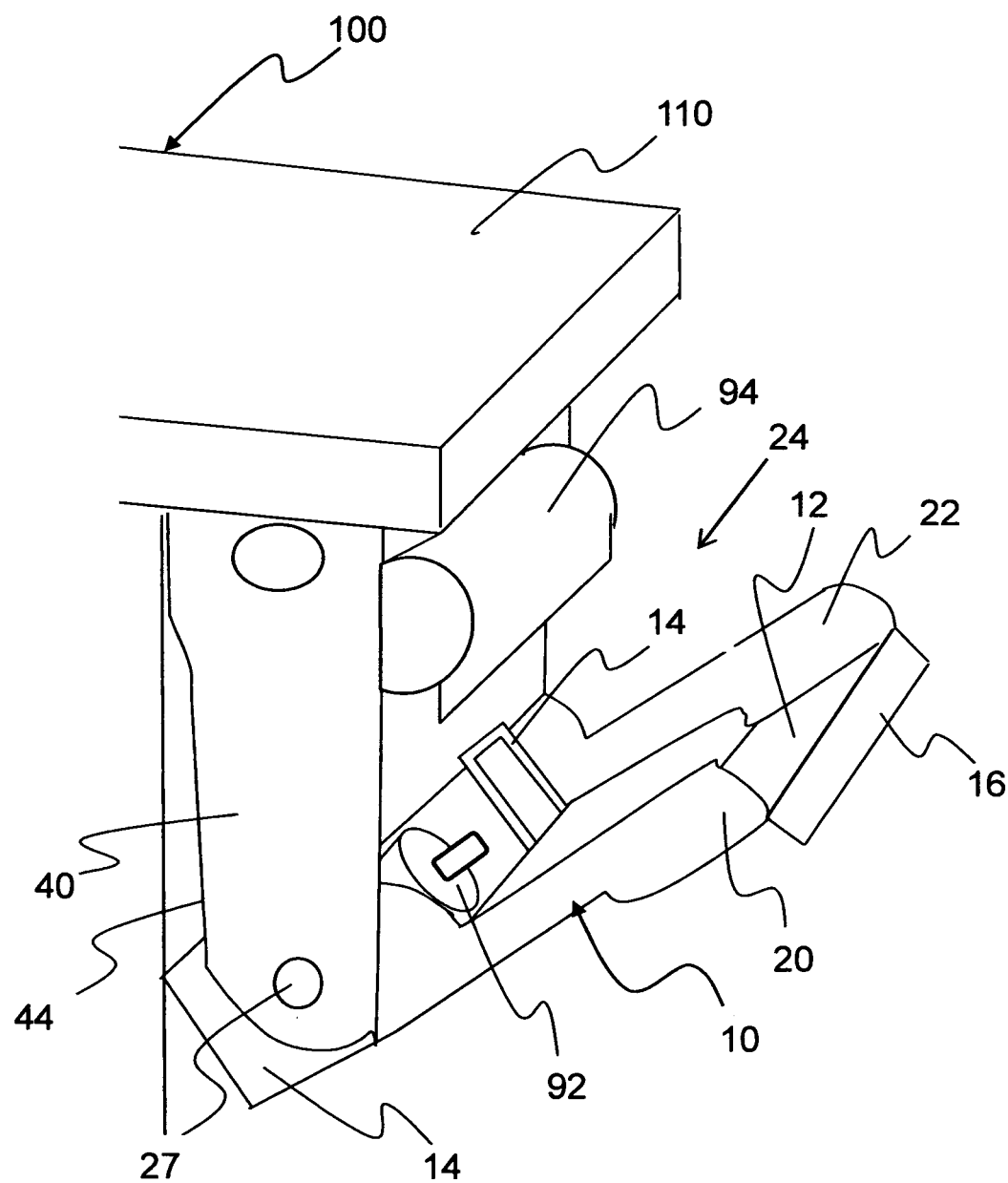

FIG. 2 shows an isometric view of an embodiment of a cooking stove container in an open orientation mounted on a grill side shelf.

Figure 3:
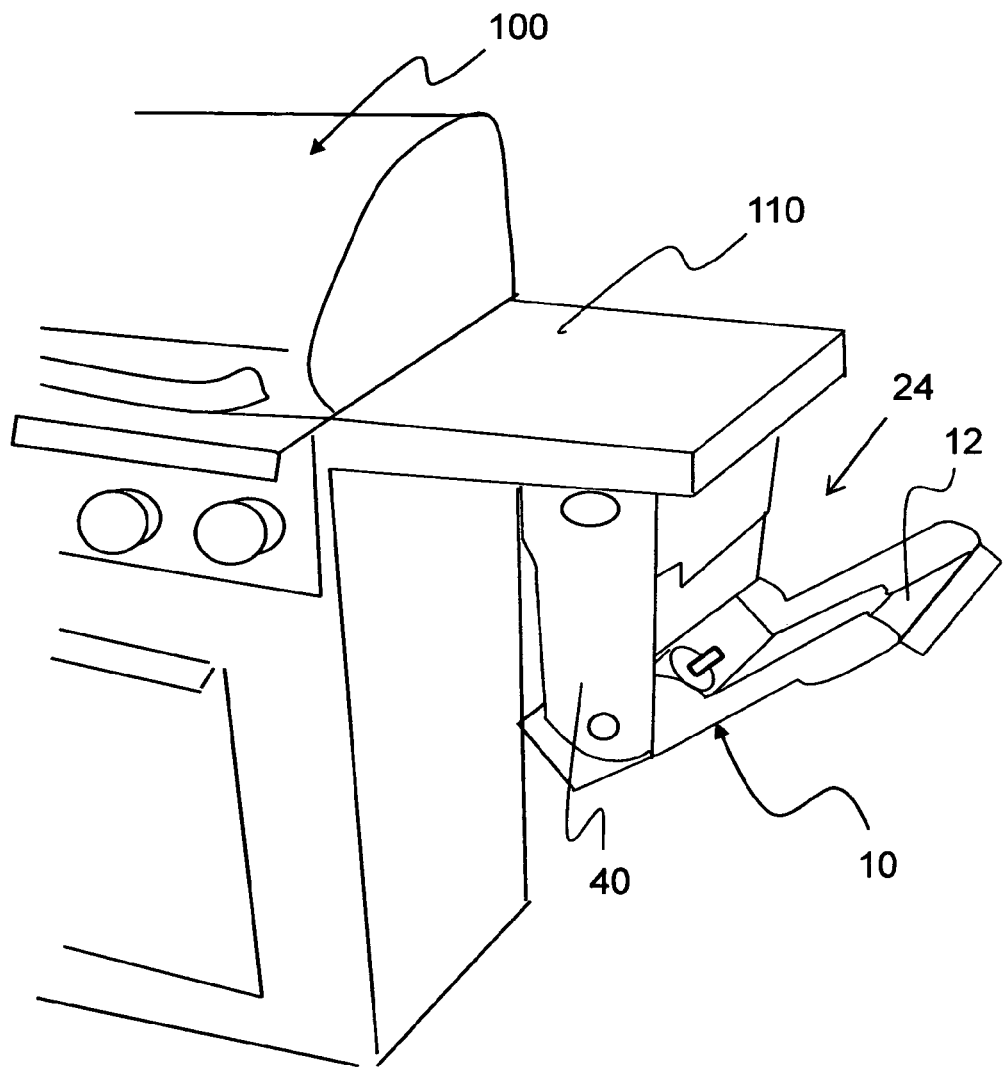

FIG. 3 shows an isometric view of an embodiment of a cooking stove container in an open orientation located under a grill side shelf.

Figure 4:
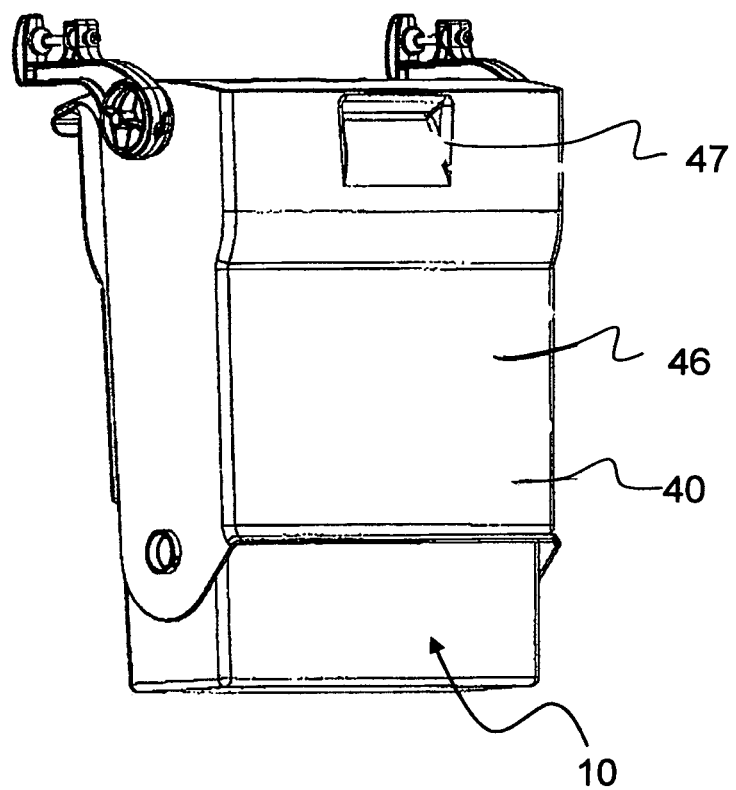

FIG. 4 shows an isometric view of an embodiment of a cooking stove container in a closed orientation.

Figure 5:
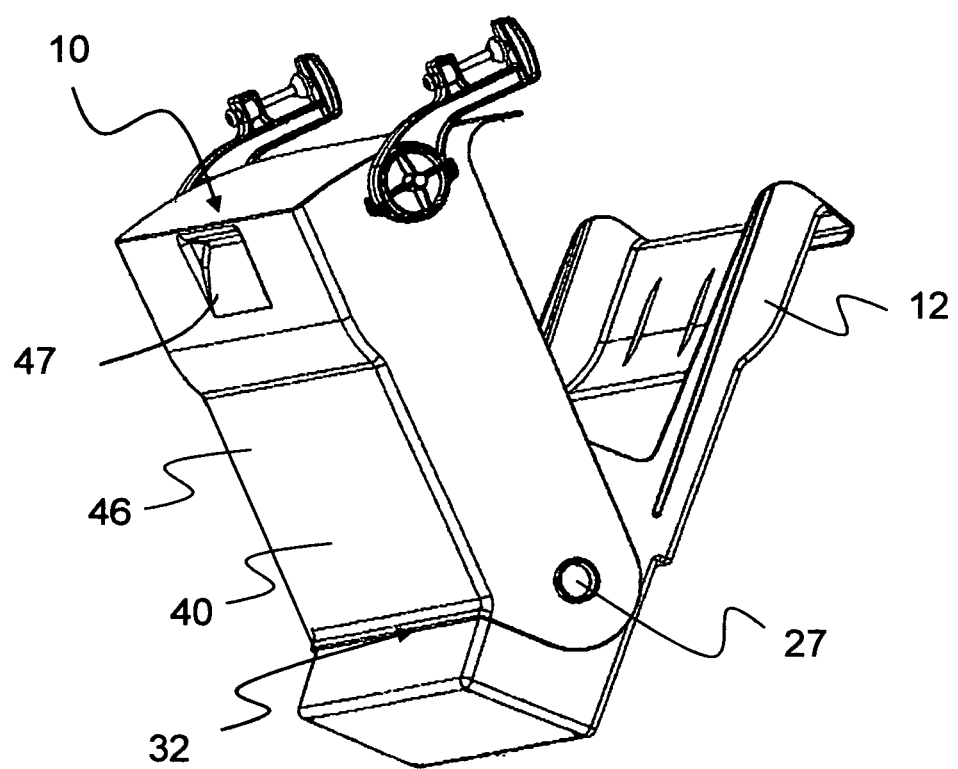

FIG. 5 shows an isometric view of an embodiment of a cooking stove container in an open orientation.

Figure 6:
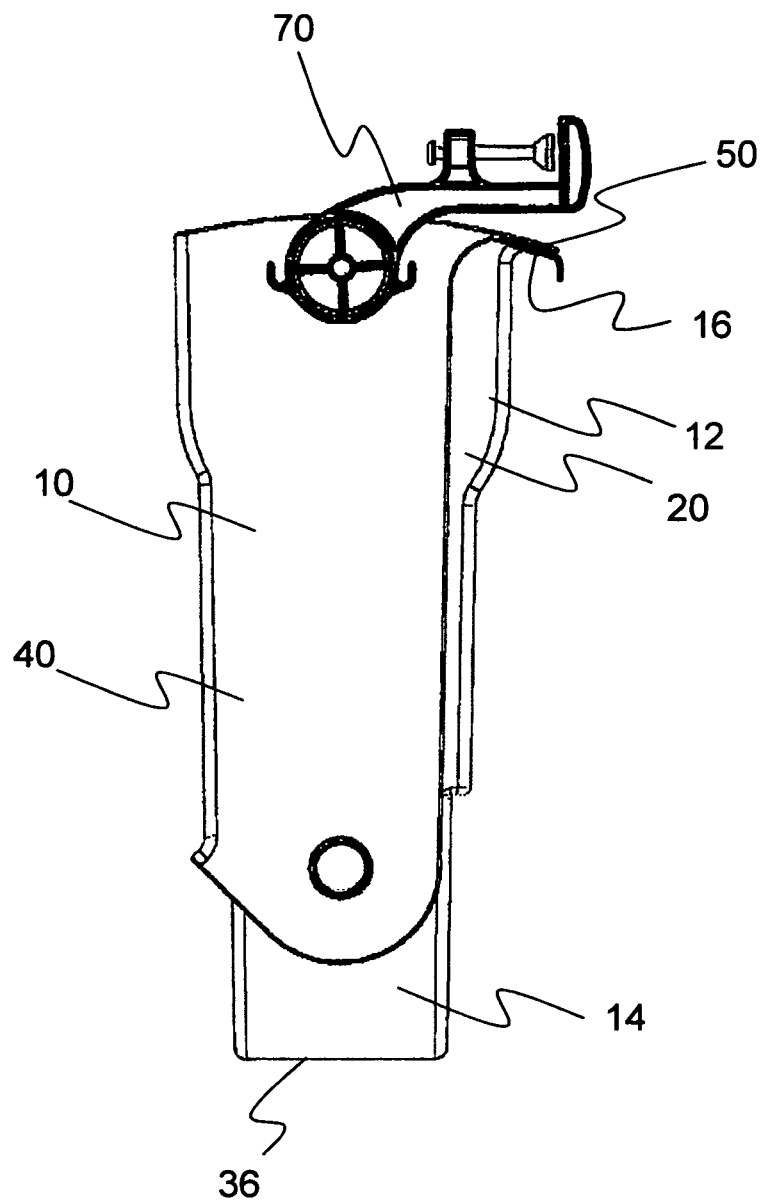

FIG. 6 shows a side view of an embodiment of a cooking stove container in a closed orientation.

Figure 7:
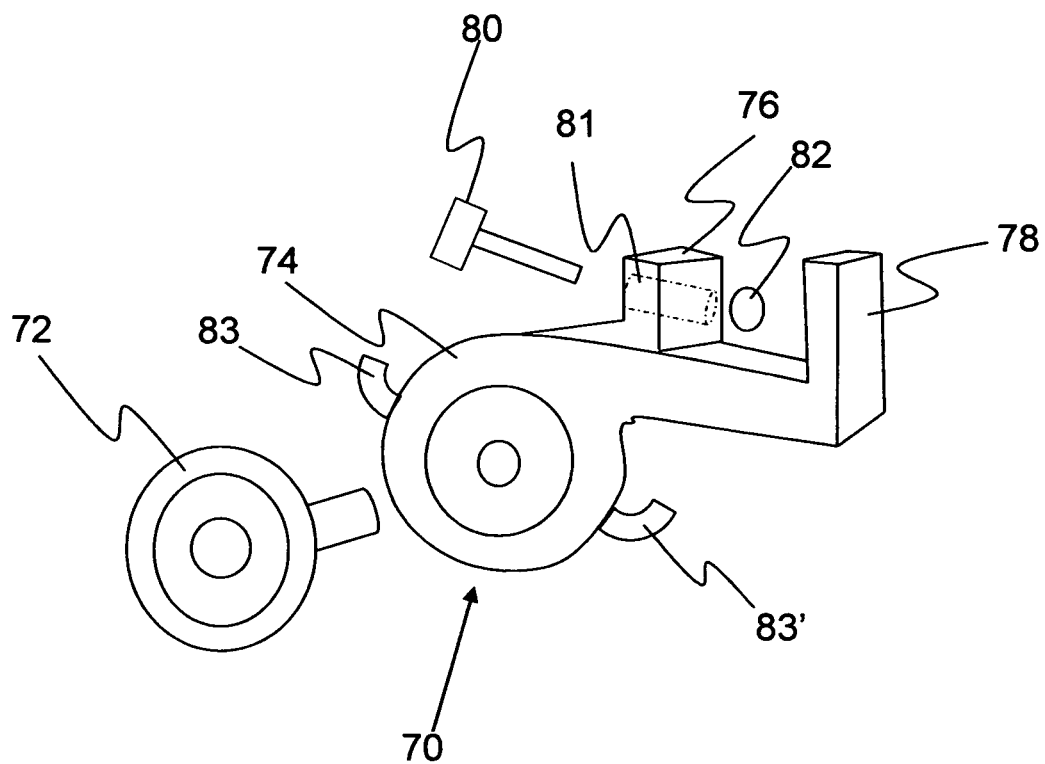

FIG. 7 shows an isometric exploded view of a mounting device according to an example embodiment of the invention.

Figure 8:
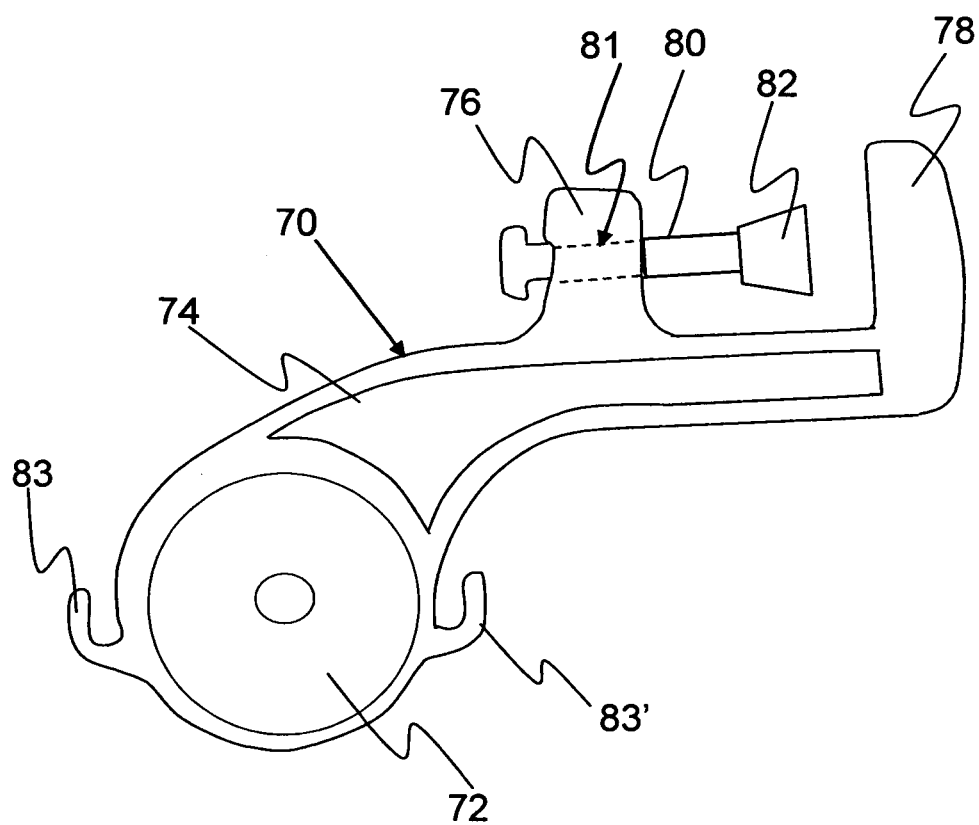

FIG. 8 shows an isometric exploded view of a mounting device with a hook according to an example embodiment of the invention.

Figure 9:
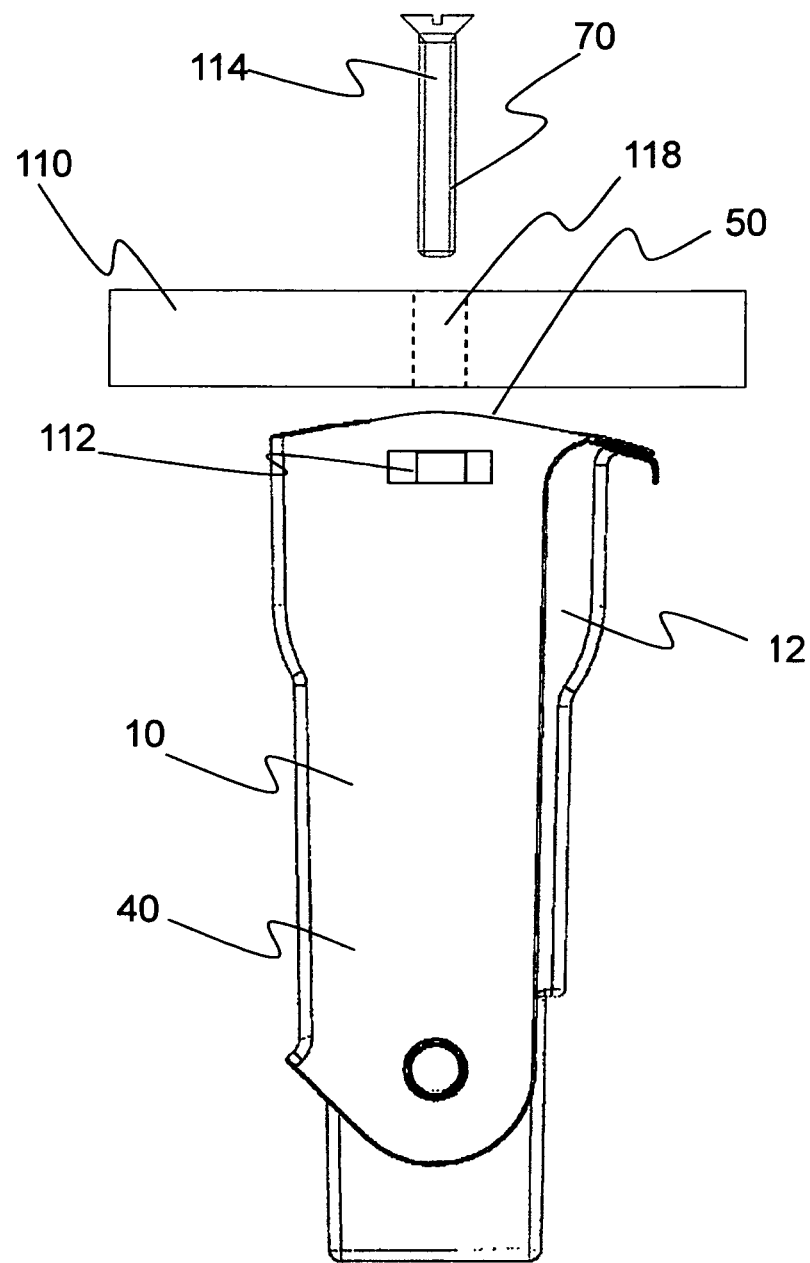

FIG. 9 shows a side view of an embodiment of a cooking stove container having a mounting device.

Figure 10:
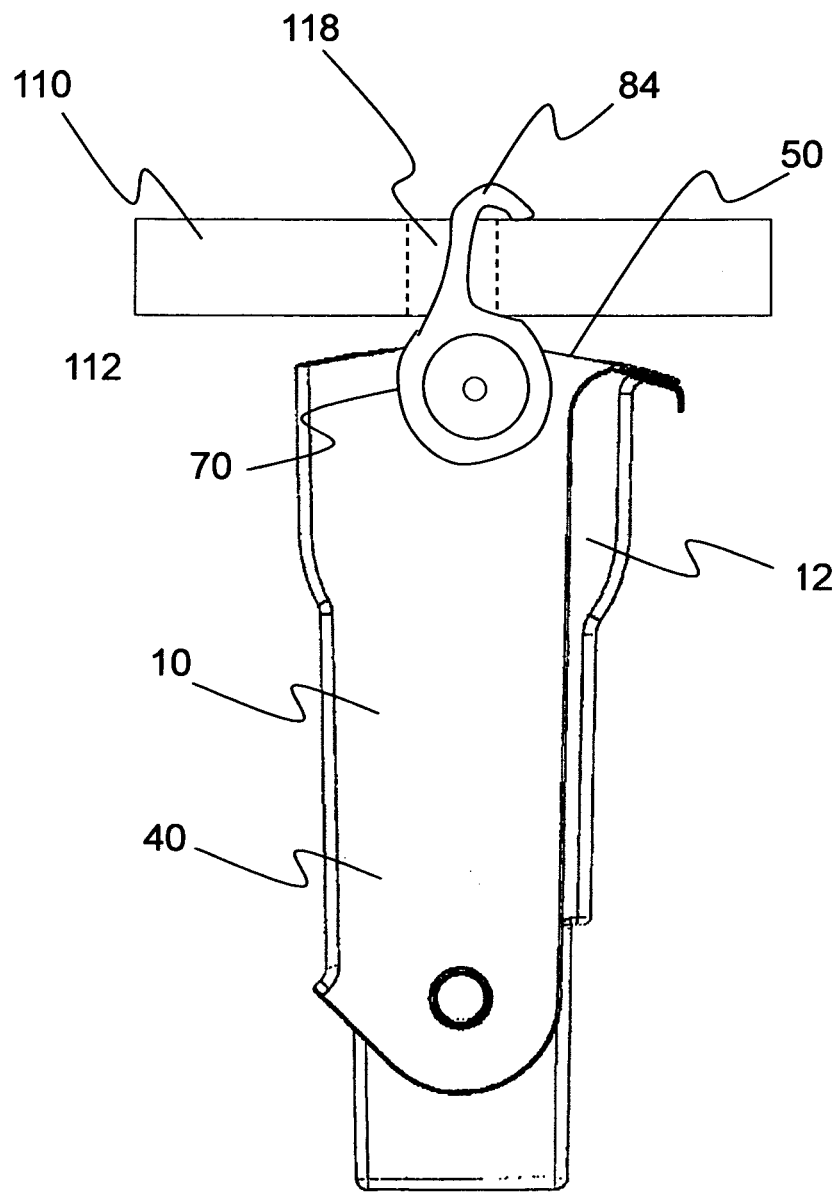

FIG. 10 shows a side view of an embodiment of a hook shaped mounting device

Figure 11:
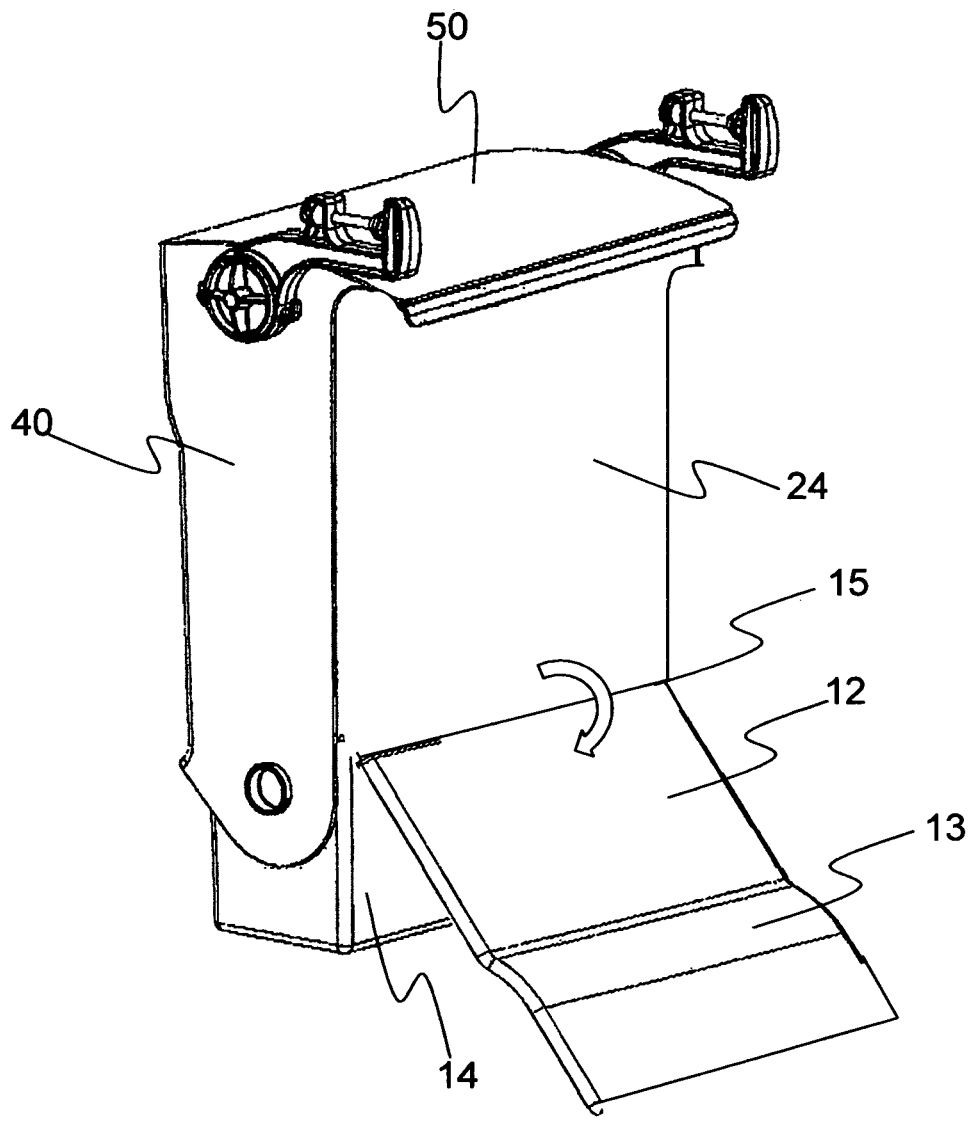

FIG. 11 shows an isometric view of an embodiment of cooking stove container having a portion of a member in an open orientation.

Figure 12:
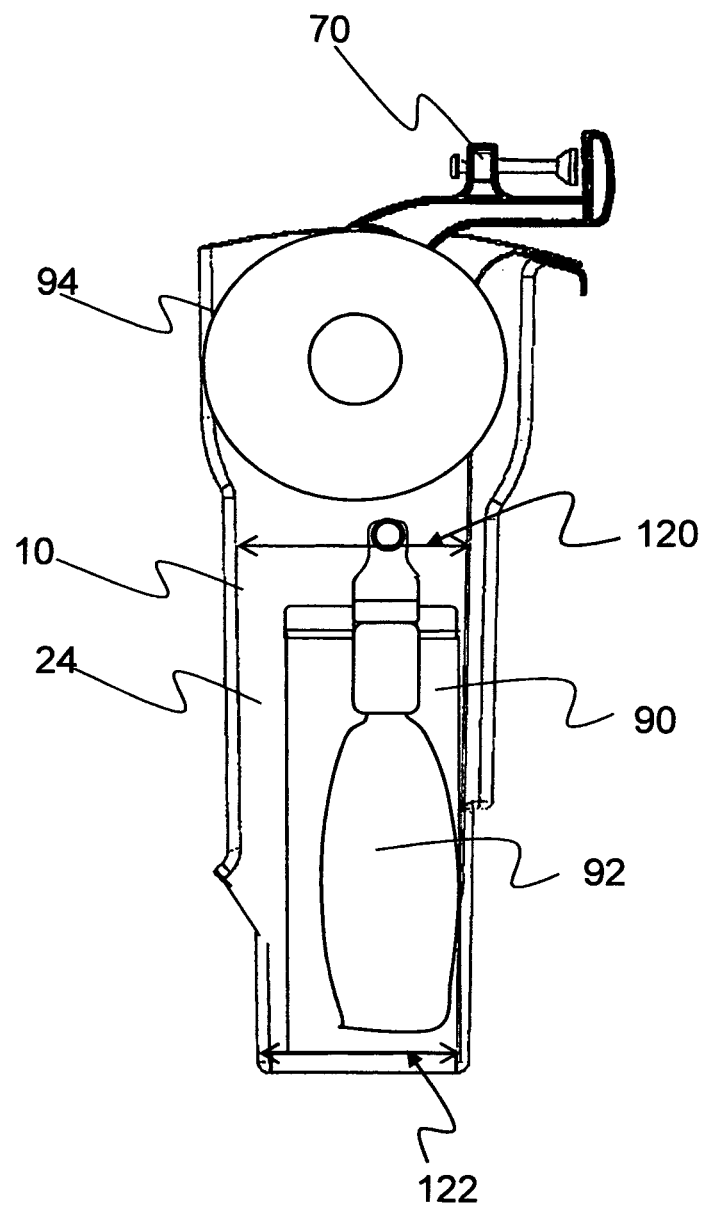

FIG. 12 shows a side cut away view of an embodiment of the cooking stove container having items stored therein.

Figure 13:
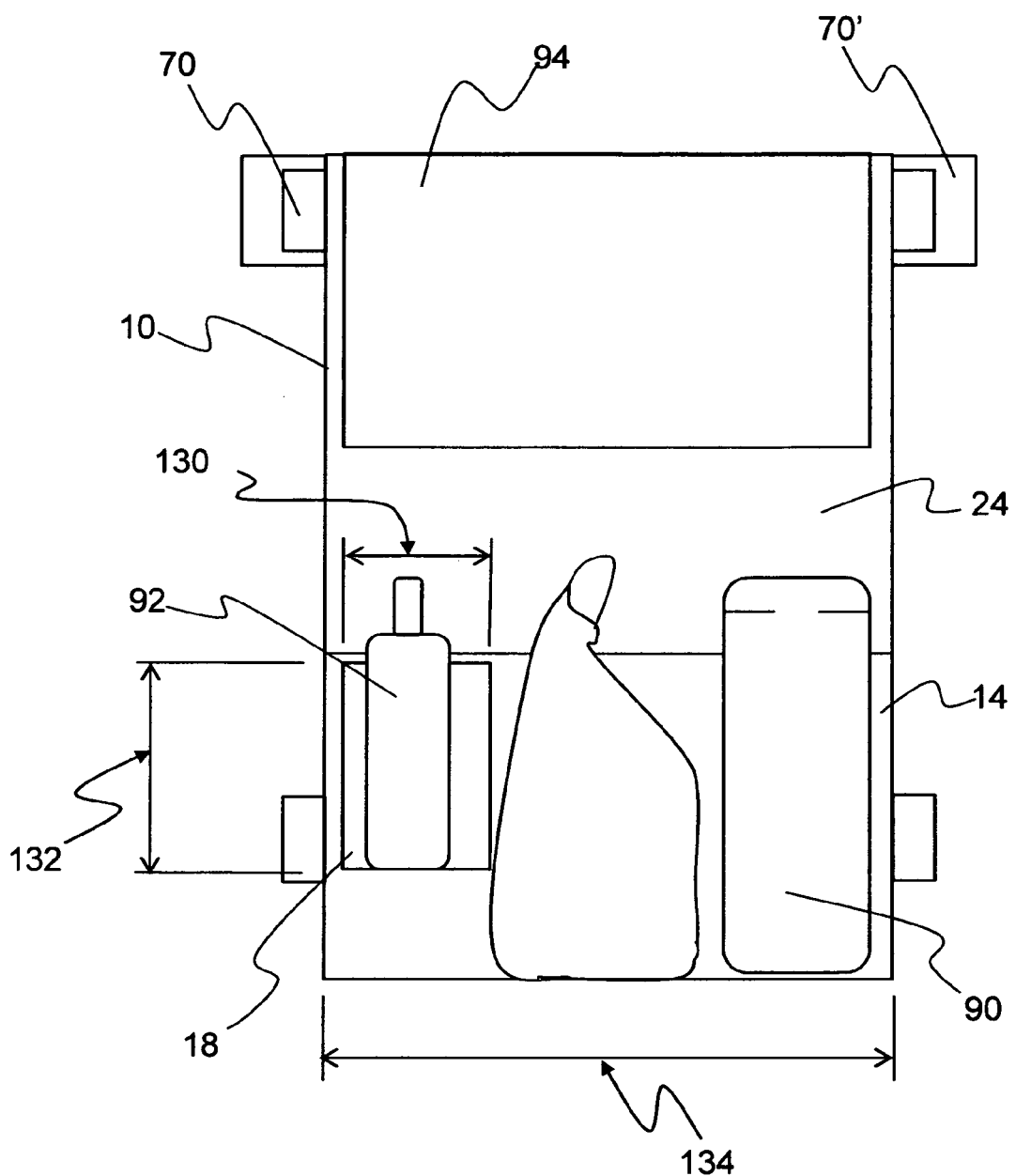

FIG. 13 shows a front cut away view of an embodiment of the cooking stove container having items stored therein.

Figure 14:
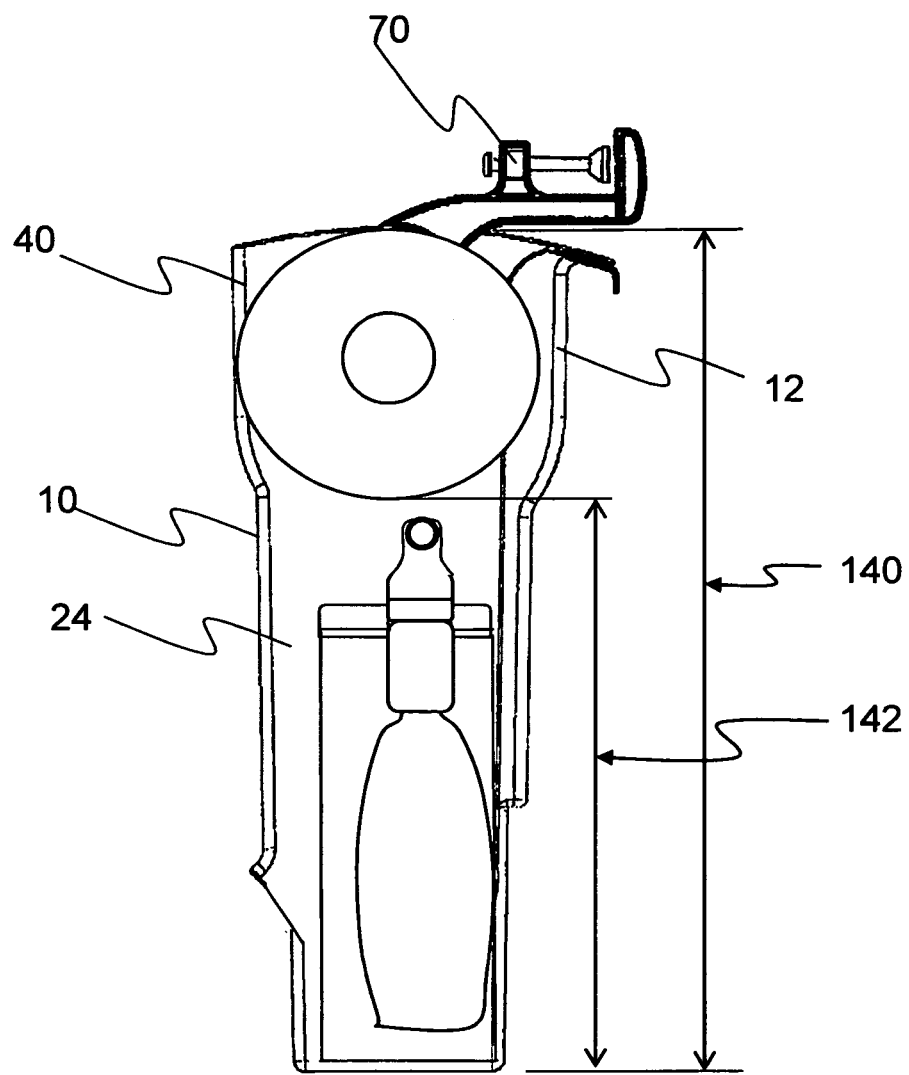

FIG. 14 shows a side cut away view of an embodiment of the cooking stove container having items stored therein.

Figure 15:
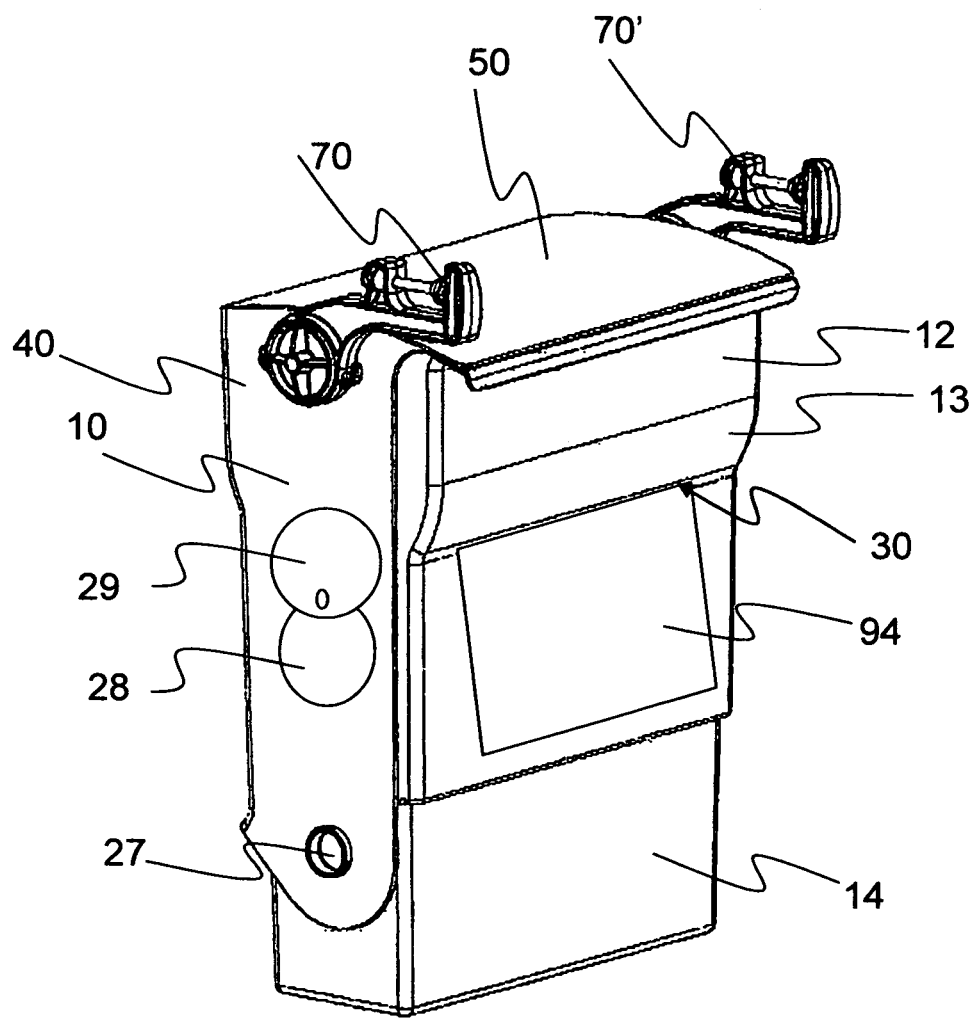

FIG. 15 shows an isometric view of an embodiment of a cooking stove container.

Reference numbers are used to indicate similar or like items throughout the figures.

DEFINITIONS

Cooking stove as used herein means a barbeque grill, a rotisserie, a spit, or any outdoor cooking apparatus where the multipurpose cooking stove container of the present invention can be mounted thereto.

Stove is defined as a portable or fixed apparatus that burns fuel or uses electricity to provide heat for cooking or heating.

Boss as used herein is defined as a protuberant part of body.

Cavity as used herein is defined as an unfilled space within a mass, especially a hollowed-out space.

Recess as used herein is defined as an indentation or cleft.

Opening as used herein is defined as something that is open, such as a breach or aperture, or an open width, or span.

Latch as used herein is defined as any various devices in which mating mechanical parts engage to fasten but usually not to lock something.

Connected with as used herein means joined or linked together either directly or through another device or assembly.

Connected to as used herein means directly attached or adjacent to.

Rainproof as used herein in reference to the cooking stove container means that the contents within the cavity of the cooking stove container will not get wet when the cooking stove container is in a closed upright orientation and exposed to a rain shower.

Rain resistant as used herein in reference to the cooking stove container means that the contents within the cavity of the cooking stove container will be effectively shielded from rain when the cooking stove container is in a closed upright orientation and exposed to a rain shower.

Example embodiments of the cooking stove container

FIG. 1 shows an example embodiment of a container according to the present invention. The container may be comprised of a back member 40, a front member 12, a tray 14 and a mounting device 70 70'. The back member 40, the front member 12 and the tray 14 form a cavity 24 as shown in FIG. 2. The mounting device 70, 70A shown in FIG. 1 is connected with the back member 40 and is adapted for attachment to a cooking stove. The tray 14 is connected with the front member 12. The back and front member may be attached at a pivoting point, 27 as shown in FIG. 2. The front member 12 may comprise a boss 26, and the back member may comprise and openings 52, 54 configured to fit over the boss 26, to create a pivot 27, as shown in FIG. 1 and FIG. 2. Any conventional means to attach the front and back member to provide pivoting motion may be used. The front member 12 may be configured to open and close with the back member 40 to allow access to the cavity 24. In addition, the front 12 and back members 40 may be configured to have an interference 32 with each other to create a stop when a member is opened a certain amount, as depicted in FIG. 2.

As shown FIG. 1, the back member 40 may be comprised of a back panel 46, a left side panel 44, a right side panel 48 and a top panel 50. The top panel 50 of the back member 40 may extend over the front member 12 when closed to protect the cavity from environmental elements such as rain, wind, dust, pollen and the like. Furthermore, the front member 12, or a portion of the front member may be configured to nest within the back member 40 as shown in FIG. 6.

The front member may comprise a lip 16 that may further comprise ridges that create an interference fit with the top panel 50 of the back member 40 when in the closed orientation as shown in FIG. 1 and FIG. 6, creating a latch. The lip may also provide a convenient means for griping the front member to opening the cooking stove container.

The back member may further comprise a towel roll support portion for securing a roll of paper towels 94 as shown in FIG. 2. The towel roll support portion may be protrusions 56 such as shown in FIG. 1, extending from the left side panel 44 and/or the right side panel 48. Any suitable means to secure a roll of paper towels would be suitable for the present invention. The cooking stove container may be configured to hold a standard six inch diameter roll of paper towels. Furthermore, the back member may have ribs on the inside surface to hold the paper towels away from the inside surface in the event of water ingress into the cavity, The front member 12, as shown in FIG. 1 may have a front left side panel 20 and a front right side panel 22 that are adjacent to the left side panel 44 and the right side panel 48 of the back member 40 when in the closed position. The front left side panel 20 and a front right side panel 22 can push against or seal against the inside of the back member 40 when closed to prevent rain water from entering the container. Furthermore, the front member 12 may have a top lip 16 that may frictionally engage with the top panel 50 of the back member 40 when in the closed position creating a latch and effectively preventing rain from entering.

The front or back member may comprise a tray for holding items such as cleaning supplies, cooking utensils, spices and the like. As depicted in FIG. 1 the tray 14 may be an integral part of the front member 12. In another embodiment however, the tray may be detached from the back or front member to provide easier cleaning. The tray may further comprise drainage holes in the bottom to allow the removal of any water. A cup 18 may be inserted into the tray to provide more secure storage of smaller items, as shown in FIG. 1, and FIG. 2. The cup may be used to hold shorter items, such as hand sanitizer. The cup may be slid along the tray to provide variable storage options. In one embodiment, two or more cups may be inserted into the tray. In another embodiment, at least one cup is connected to the tray.

In addition, as depicted in FIG. 15 the cooking stove container may further comprise a cavity opening 28 for access to, for example, hand sanitizer. A cavity opening cover 29 may be configured to seal the cavity opening 28, when not in use, as depicted in FIG. 15.

The cooking stove container may comprise a towel roll support in the front of back member. As depicted in FIG. 2, paper towels 94 may be attached to the back member and may be easily accessible when the container is in the open orientation. In another embodiment, the leading edge of the paper towels may fit through a towel opening 30 in the container to provide access to paper towels 94 when the container in the closed orientation, as depicted in FIG. 15.

The cooking stove container may be part of a cooking stove, as depicted in FIG. 3, or it may connected with a cooking grill by a mounting device 70. The mounting device may be any suitable configuration for attachment to a cooking stove or cooking stove side shelf. The mounting device may simply hook to openings in cooking stove side shelf or may comprise a means to bolt through or onto a portion of the cooking stove.

The cooking stove container 10 as depicted in FIG. 4 comprises a handle 47 in the back panel 46 of the back member 40. A handle may also be configured into the front member, to allow easier opening and closing of the cooking stove container. The handle may be a recess as shown in FIG. 4, and the recess may be molded or otherwise formed into the member. The handle may also be a protrusion from a member, such as a knob or curved member that is attached to a member or panel.

The cooking stove container 10 depicted in FIG. 5 is in the open orientation. The front member 12 is pivoted away from the back member 40 about the pivot 27. The front member 12 and back member 40 have an interference 32 that limits how far the two members can pivot and open. The front member is more narrow in the embodiment shown in FIG. 5, and nests within the back member 40 when in the closed orientation, as shown in FIG. 6.

The cooking stove container 10 may be configured to be resistant to environment elements as depicted in FIG. 6. A portion of the front member 12, such as the side panel 20, may be configured to nest within the back member, as depicted in FIG. 6. The top panel 50 of the back member 40 may be further configured to overhang the front member 12 to prevent water ingress into the cavity. In addition, the cooking stove container 10 may comprise holes 36 in the bottom to allow water to flow out of the cavity, as depicted in FIG. 6. The cooking stove container may be configured to be rainproof, and in an alternative embodiment, the cooking stove container may be configured to be rain resistant as defined herein.

The mounting device 70 as depicted in FIGS. 7 and 8 may comprise a bracket 74 having a first jaw 76 and second jaw 78, whereby a portion of the cooking stove may be place between the two jaws. A threaded bolt 80 may be positioned through the threaded opening 81 in the first jaw 76, and be turned to secure the cooking stove portion between the first and second jaw. A stopper 82 may be attached to the end of the threaded bolt to provide more secure attachment. The bracket 74 may further comprise a utensil hook 83 or hooks 83' for hanging cooking utensils and the like. The utensil hooks may be attached to any portion of the cooking stove container. A knob screw 72 may be used to attach the bracket 74 to the cooking stove container 10. In addition, as shown in FIG. 1, the bracket 74 or boss 140 may be configured to provide additional degrees of freedom to the mounting device 70, therein allowing the mounting device to be more easily oriented to the cooking stove. The bracket 74, and/or the boss 140 may be configured with teeth, such as radial teeth as shown on the boss 140 in FIG. 1, to allow the bracket to be rotated.

The mounting device may have any dimensions that provide for effective clamping to cooking stoves. For example, the threaded bolt may be adjusted to accept cooking stove portions up to approximately 1.07 inch in dimension. The bracket clamping surface may be crowned to conform to curved attachment portions. The brackets 74 may be reversed to mount the cooking stove container away from the grill side shelf. The mounting device can be assembled using a Phillips screwdriver and 1.25 inch clearance under the tray. Mounting brackets can be 0.75 inch wide and 13.125 inches apart. Depending on the flexibility of the cooking stove portion attached, the cooking stove container 10 may be removed from the mounting devices 70, 70' by removing two hand-tightened knob screws 72. The mounting device may be configured to be attached using any conventional tool and preferable any conventional hand tool including but not limited to a wrench, or screwdriver and the like. In one embodiment, the mounting device may be attached to the grill by hand.

An alternative mounting device 70 depicted in FIG. 9 comprises a first mounting portion 114, such as a bolt, that may be passed through an opening in the cooking stove 118, and secured by a second mounting portion 112, such as a nut.

A very simple mounting device 70 may comprise a mounting hook 84, that may be positioned through an opening 118 in the side shelf 110 of the cooking stove. The mounting hook 84 may also be hooked over a tube or any extension of the cooking stove. The mounting hook may be connected with the container using the bracket configurations as previously described. For example, the hook 84 could attach to a boss 140 and be secured with a knob screw 72. Any suitable mounting device may be used to mount the cooking stove container to a cooking stove.

The cooking stove container depicted in FIG. 11 comprises a moveable connection 15 that enables a portion of the front member 12 to open. The moveable connection may comprise at least one hinge, or living hinge. In an alternative embodiment, a portion of a member may be configured to slide open.

FIG. 12 depicts a cross sectional side view of a cooking stove container. The cooking stove container 10 depicted in FIG. 12 comprises cleaner 90, hand sanitizer 92, and paper towels 94 within the cavity 24.

The cooking stove container may have any suitable dimensions. The depth dimensions of the cavity 24 are depicted in the tray area as 122, and higher in the cavity as 120 in FIG. 12. The depth in the tray area 122, may be approximately 4.06 inches, and the depth 120 higher up in the cavity may be 4.89 inches. As shown in FIG. 13, the cooking stove container 10 may be 11.13 inches wide 134. In addition, the cup 18 may be 3.16 inches wide 130 by 5.08 inches high 132, as depicted in FIG. 13. The height 140 of the cooking stove container 10 as depicted in FIG. 14 may be 18.72 inches, and the height from the base to the paper towel 142, may be 11.325 inches. All Dimensions are only non-limiting example dimensions and can be varied according to the actual requirements of the container. For example the dimensions can be plus or minus 10% or plus or minus 30%, or plus or minus 50%. These dimensions are provided in Table 1. Combinations of dimensions provided in Table 1 may be used.

TABLE 1

| | Width Ref. # 134 | Cup Width Ref. # 130 | Cup Height Ref. # 132 | Depth Ref. # 120 | Depth Ref. # 122 | Height Ref. # 140 | Height Ref. # 142 |
| --- | --- | --- | --- | --- | --- | --- | --- |
| Dimensions of container (inch) | 11.13 | 3.16 | 5.08 | 4.89 | 4.06 | 18.72 | 11.33 |
| Dimensions +10% | 12.24 | 3.48 | 5.59 | 5.38 | 4.47 | 20.60 | 12.46 |
| Dimensions +30% | 14.47 | 4.11 | 6.60 | 6.36 | 5.28 | 24.34 | 14.72 |
| Dimensions +50% | 16.70 | 4.74 | 7.62 | 7.34 | 6.09 | 28.08 | 16.99 |
| Dimensions −10% | 10.02 | 2.84 | 4.57 | 4.40 | 3.65 | 16.85 | 10.19 |
| Dimension −30% | 7.79 | 2.21 | 3.56 | 3.42 | 2.84 | 13.11 | 7.93 |
| Dimension −50% | 5.57 | 1.58 | 2.54 | 2.45 | 2.03 | 9.36 | 5.66 |

The cooking stove container of the present invention may be made out of any suitable material including but not limited to metal, plastic, composites, or any combination thereof and the like. The cooking stove container may be made out of materials that are weather and in particular water resistant.

The above and below advantages and features are of representative embodiments only, and are not exhaustive and/or exclusive. They are presented only to assist in understanding the invention. It should be understood that they are not representative of all the inventions defined by the claims, to be considered limitations on the invention as defined by the claims, or limitations on equivalents to the claims. For instance, some of these advantages may be mutually contradictory, in that they cannot be simultaneously present in a single embodiment. Similarly, some advantages are applicable to one aspect of the invention, and inapplicable to others. Furthermore, certain aspects of the claimed invention have not been discussed herein. However, no inference should be drawn regarding those discussed herein relative to those not discussed herein other than for purposes of space and reducing repetition. Thus, this summary of features and advantages should not be considered dispositive in determining equivalence. Additional features and advantages of the invention will become apparent in the following description, from the drawings, and from the claims, Unless explicitly stated otherwise, each numerical value and range should be interpreted as being approximate as if the word about or approximately preceded the value of the value or range.

Given the variety of embodiments of the present invention just described, the above description and illustrations should not be taken as limiting the scope of the present invention defined by the claims.

While the invention has been particularly shown and described with reference to the preferred embodiments thereof, it will be understood by those skilled in the art that various changes in form and details may be made without departing from the spirit and scope of the invention. It is intended to cover various modifications and similar arrangements and procedures, and the scope of the appended claims therefore should be accorded the broadest interpretation so as to encompass all such modifications and similar arrangements and procedures.

We claim:

1. A multipurpose cooking stove container comprising:
   a. a back member;
   b. a front member;
   c. a tray;
   d. a mounting device comprising at least one bracket for detachably attaching said multipurpose cooking stove container to the underside of a side shelf of a cooking stove, comprising:
      i. a first jaw;
      ii. a second jaw, whereby a portion of a cooking stove side shelf may be placed between said first jaw and said second jaw; and
      iii. a bolt positioned through a threaded opening in the first jaw whereby the bolt may be turned to secure said portion of a cooking stove side shelf between the first and second jaw,
   wherein said back member, front member, and tray are configured to form a cavity, wherein said back member is connected with said front member, wherein said multipurpose cooking stove container is configured to close and open to allow access to said cavity, and wherein said front member and back member are discrete pieces connected at a pivot and configured with an interference that limits the amount the said front member can pivot open.

2. The multipurpose cooking stove container of claim 1 wherein the front member is configured to open and close with said back member about the pivot to allow access to the cavity.

3. The multipurpose cooking stove container claim 1 wherein at least one member is configure to move about the pivot to enable opening and closing of the container.

4. The multipurpose cooking stove container of claim 3 wherein the pivot comprises an opening in the front or back member and a boss in the other member.

5. The multipurpose cooking stove container of claim 1 wherein a portion of the front member is configured to open and close to allow access to the cavity.

6. The multipurpose cooking stove container of claim 1 wherein the tray is attached to the front member.

7. The multipurpose cooking stove container of claim 1 wherein the tray further comprises compartments for retaining objects.

8. The multipurpose cooking stove container of claim 1 further comprising at least one cup.

9. The multipurpose cooking stove container of claim 8 wherein the cup is attached to the tray.

10. The multipurpose cooking stove container of claim 1 further comprising a towel support.

11. The multipurpose cooking stove container of claim 1 further comprising a towel support and a towel opening in a member.

12. The multipurpose cooking stove container of claim 1 wherein the back member comprises:
    a. a left side panel;
    b. a right side panel;
    c. back panel; and
    d. top,
    wherein the top panel extends over said front member when closed.

13. The multipurpose cooking stove container of claim 1 wherein the container is configured to protect the cavity from environmental elements.

14. The multipurpose cooking stove container of claim 1 wherein the container has at least one cavity opening configured to allow access to the cavity, when the front member and back members are configured in a closed orientation.

15. The multipurpose cooking stove container of claim 14, wherein the back member comprises a left and a right side panel, and wherein the said cavity opening is configured in a side panel.

16. The multipurpose cooking stove container of claim 1 further comprising at least one utensil hook.

17. A cooking stove comprising at least one side shelf and a multipurpose cooking stove container located under said side shelf comprising:
    a. a back member;
    b. a front member;
    c. a tray; and
    d. a mounting device comprising at least one bracket for detachably attaching said multipurpose cooking stove container to the underside of said side shelf of a cooking stove, comprising:
       i. a first jaw;
       ii. a second jaw, whereby a portion of said cooking stove side shelf may be placed between said first jaw and said second jaw; and
       iii. a bolt positioned through a threaded opening in said first jaw whereby said bolt may be turned to secure a portion of the cooking stove side shelf between said first and second jaw,
    wherein said back member, said front member, said tray form a cavity, and wherein said back member is connected with said front member, wherein said multipurpose cooking stove container is configured to close and open to allow access to said cavity and wherein said front member and back member are discrete pieces connected at a pivot and configured with an interference that limits the amount said front member can pivot open.

18. The multipurpose cooking stove container of claim 17 further comprising a knob screw having teeth configured for detachably fastening said bracket to the cooking stove container whereby the bracket may be rotated about and locked into a position by said knob screw, therein allowing the bracket to be suitably oriented to the cooking stove.

* * * * *